United States Patent [19]

Sadeh et al.

[11] 4,243,749

[45] Jan. 6, 1981

[54] IMMUNOASSAY EMPLOYING AN ENZYME LABEL

[75] Inventors: Dora Sadeh, Tel Aviv; Charles S. Hexter, Rehovot, both of Israel

[73] Assignees: Miles Yeda Ltd., Rehovot, Israel; Hypolab S.A., Coinsins, Switzerland

[21] Appl. No.: 887,328

[22] Filed: Mar. 16, 1978

[30] Foreign Application Priority Data

Mar. 16, 1977 [IL] Israel .................................. 51667

[51] Int. Cl.$^2$ ..................... G01N 31/00; G01N 31/14; G01N 33/16

[52] U.S. Cl. .................................... 435/7; 23/230 B; 424/8; 424/12; 424/13

[58] Field of Search .................. 23/230 B; 424/8, 12, 424/13; 435/7

[56] References Cited

U.S. PATENT DOCUMENTS

| | | | |
|---|---|---|---|
| 3,998,943 | 12/1976 | Ullman | 424/12 |
| 4,017,597 | 4/1977 | Reynolds | 195/103.5 |

OTHER PUBLICATIONS

Feldmann et al., (Ed.), Immunoenzymatic Tech., Proc. 1st Int. Sym. on Immunoenzym, Tech., North Holland/Amer. Elsevier Pub. Co. N.Y., 1976 pp. 125-133.
Clin. Chem., vol. 22, 1976 pp. 1243-1255.

*Primary Examiner*—Anna P. Fagelson
*Attorney, Agent, or Firm*—Browdy and Neimark

[57] ABSTRACT

According to the present invention there is provided a sensitive quantitative assay for the determination of a hapten "X" which comprises: preparing a conjugate of the hapten X which conjugate is adapted to ellicit antibody formation, and injecting a mammal with said conjugate, resulting in a specific antibody against the said hapten, "anti-X"; preparing a conjugate of the hapten X and of another entity Y, which is either another hapten or a larger molecule, injecting a mammal with the entity Y if it is a larger molecule, or with a conjugate thereof if it is a small molecule which does not by itself ellicit antibody formation, so as to form anti-Y antibodies, preparing a conjugate of a suitable enzyme and the antibody against Y, i.e. an (enzyme)-(anti-Y)-conjugate; adsorbing the antibodies against X, i.e. anti-X on a solid support, contacting said solid support with a mixture containing the unknown quantity of hapten X and a known quantity of the X-Y conjugate; removing unreacted X and X-Y, leaving all anti-X sites occupied, adding enzyme-labelled anti-Y antibody; adding a suitable substrate resulting in a color reacting and measuring the intensity of color indicating the quantity of bound enzyme and deducing from calibration curves the quantity of the hapten X; and to a kit for carrying out such assay.

11 Claims, No Drawings

IMMUNOASSAY EMPLOYING AN ENZYME LABEL

FIELD OF THE INVENTION

The present invention relates to a sensitive quantitative assay method for the determination of various haptens. More specifically, the invention relates to a novel enzyme immunoassay for determination of haptens is the pico-gram range, which is based ultimately on a sensitive color reaction. The novel assay is adapted for use in the determination of various types of haptens. It is of special value in the quantitative determination of various hormones, such as estrogens, prostaglandins, thyroxine; of polypeptides, vitamins, glycosides, and the like. The present invention further relates to a kit for effecting such quantitative measurements and to certain novel components of such kits and for use in the novel assay.

BACKGROUND OF THE INVENTION

Many methods have been developed for the qualitative and quantitative determination of low molecular weight substances such as hormones and the like. Amongst the most sensitive are those based on proteins capable of binding specifically the substance to be determined. A very sensitive test is the radio-immunoassay in its variations. Radio immunoassays have the drawback that the labelled entity has a comparatively short shelf-life, that there exist severe regulations concerning the handling of radioactive materials and that highly qualified personnel must be used for performing such assays. A multitude of Enzyme-Immunoassays is known, and part of these is summarized in the review of this subject in Clinical Chemistry 22 (1976) 1243–1255.

The present invention provides a sensitive and convenient quantitative assay for the determination of small molecules (haptens) such as hormones, vitamins, glycosides, etc. Haptens are defined as protein-free substances whose chemical configuration is such that they can react with specific antibodies but are themselves not capable of causing the formation of antibodies. In order to produce antibodies against specific haptens, such haptens must be first coupled to macromolecules and the resulting conjugate is injected into suitable test animals.

SUMMARY OF THE INVENTION

The invention relates to a quantitative assay of high sensitivity for determination of haptens. There is prepared a specific antibody to the hapten which is being assayed, and this antibody is insolubilized on a solid support. There is carried out a competition reaction between the unknown sample and a hapten conjugate. The quantity of the hapten conjugate bound to the solid support is inversely proportional to the quantity of free hapten in the sample which is assayed. The determination is effected by reaction of an enzyme-labelled antibody to the macromolecular or small molecule portion of the conjugate, followed by reaction with a suitable substrate resulting in a color reaction.

The method according to the present invention can be schematically described as follows:

a. A hapten (as defined above, and preferably a hormone) designated as "X", is to be determined.
b. The hapten is bound to a compound adapted to ellicit antibody formation, and this is injected into a test animal resulting in the production of anti-X.
c. A conjugate is formed of X and of another substance, Y.
d. Substance Y or a Y-conjugate is injected into animals and anti-Y is produced.
e. There is produced a conjugate of anti-Y and of a suitable enzyme, i.e. enzyme-anti-Y.

The assay is performed as follows:

(1) Anti-X, i.e. the antibody to the substance X which is to be determined, is adsorbed on a suitable solid support, and thus insolubilized. Amongst others, there may be used polystyrene, and the preferred form is one of small test tubes which are coated on the inside with the anti-X antibody.

(2) The sample containing an unknown quantity of X and a known quantity of X-Y conjugate are contacted with the solid and the anti-X adsorbed thereon, resulting in a competition reaction of X and X-Y with the anti-X. The quantity of X and X-Y are chosen in such a manner that all active anti-X sites are occupied either by X or by the X of X-Y.

(3) The system is washed to remove any unreacted X and X-Y.

(4) Enzyme labeled anti-Y is added, and this reacts with all the Y sites of the bound X-Y conjugate.

(5) Excess of enzyme-labelled anti-Y is washed off.

(6) A suitable substrate is added resulting in a color reaction indicative of the quantity of the bound enzyme.

By preparing a calibration curve or by running simultaneously a number of samples, containing known quantities of X, the quantity of X in the sample which is being assayed is determined. It is clear that the quantity of hapten conjugate X-Y bound to the solid support is inversely proportional to the amount of free hapten in the sample.

Amongst substances which can be determined in very low concentrations there may be mentioned various steroids such as estrogens, progestins, etc, prostaglandins, $PGF_{2\alpha}$, $PGE_2$, etc., thyroid harmones, such as thyroxine, triiodothyronine, etc., cardiac glycosides, such as digoxin, digitoxin, etc., vitamins such as vitamin $B_{12}$, etc., drugs, such as diphenylhydantoin, morphine, etc.

Suitable substances for use as Y-moieties are, for example, trinitrophenyl-lysine, sulfanilic acid, p-aminobenzoic acid, p-azo-phenyl-$\beta$-lactoside, hippuric acid, iodoacetylamino-benzene-azo-hippuric acid, 6-carboxypurine, 5-acetyl uracil, thymidin, iridine.

It is clear that the above description is schematical, the assay steps can also be described as incubation of standards and hapten-conjugate in antibody-coated tubes (or other form of coated surface), decantation and incubation with enzyme-labelled antibody, decantation and addition of enzyme substrate solution, determination of absorbance. Quantities of hormones which can be quantitatively determined are in the picogram range. The sensitivity and accuracy is adequate for all requirements of such determinations for medical purposes.

For carrying out the novel method no radioactive material and no equipment for handling such material is required. Various haptens can be determined in a convenient manner. Amongst these there may be mentioned hormones such as steroids, prostaglandins, thyroid hormones; peptides, polysaccharides, vitamins, cardiac glycosides, etc. The enzyme-labelled antibody required is easily prepared and may be used for all such low-molecular-weight compounds. The reagents are stable, can be stored without any appreciable deterioration over a comparatively prolonged period of time and thus kits for carrying out the novel assay can be prepared and marketed. The instrumentation required is simple and readily available in clinical laboratories.

The invention is illustrated with reference to the following examples which are intended to illustrate the invention and which are not to be construed in a limitative sense.

EXAMPLE 1: Determination of Serum Estradiol

A. Method Using Estradiol-ε-DNP Lysine (Estradiol-6-ε-dinitrophenyl lysine)

1. Assay description

A quantity of estradiol-6-ε-DNP lysine conjugate is added to a sample containing estradiol and the mixture is incubated in a polystyrene tube that has been coated with anti-estradiol. The amount of estradiol-DNP bound to the tube is inversely proportional to the amount of free estradiol in the sample. The actual quantity of estradiol-DNP is determined through the use of peroxidase labeled anti-DNP antibodies, followed by addition of peroxidase substrate and colorimetric reading.

2. Materials a. Anti-estradiol antiserum was prepared by immunization of a goat with 17ε-estradiol-6-carboxymethyl-bovine serum albumin. The goat was injected intradermally with 2 mg of antigen in complete Freund's adjuvant and given boosters after 30 days and 60 days and bled on the 8th day after the last booster.

b. Anti-dinitrophenyl antiserum (anti-DNP) was prepared by immunizations of rabbits with dinitrophenyl-bovine serum albumin. The rabbits were injected with 1 mg of antigen in complete Fruend's adjuvant and boosters given and bled exactly as above.

c. The gamma globulin fractions of anti-DNP-BSA anti-serum were isolated by ammonium sulfate precipitations, followed by DEAE-cellulose chromatography and purified from anti-BSA antibodies by immunoadsorption on BSA-agarose (6 mg/ml) columns. Horseradish peroxidase (Miles 1 Grade) was coupled to the lgG fraction of anti-DNP serum with glutaraldehyde. The peroxidase conjugate was then purified by chromatography on Sephadex G-200 columns and the molar ratio of peroxidase to lgG was determined by U.V. absorption. The conjugates used in the assay had molar ratio 0.8-1.

d. Hapten conjugate estradiol-6-ε-DNP lysine was prepared from estradiol-6-carboxymenthyl oxime and ε-dinitrophenyl lysine using N-Hydroxysuccinimide. The product was evaluated spectrophotometrically by recording U.V. absorption spectra at 260 nm for steroid oxime residue and at 360 nm for DNP molecule. The molar ratio of estradiol to ε-DNP lysine was found to be 1.0. The product was also evaluated by radioimmunoassay with anti-estradiol-BSA antiserum.

e. The gamma globulin fraction of anti-estradiol-6-BSA serum was isolated by chromatography on DEAE cellulose and purified by immunoadsorption from anti-BSA antibodies. The absence of BSA antibodies was verified by immunoelectrophoresis, and the potency of the anti-serum as well as specificity versus estradiol was evaluated by radioimmunoassay. The purified fraction of anti-estradiol is used in the assay as coating solution for preparation of antibody coated polystyrene surface.

f. Polystyrene tubes (75×12 mm, Lab-Tek Cat. 4411) are used as solid support.

g. Estradiol (Ikapharm Code 1995) is used as standard antigen.

h. Substrate used for enzymatic reaction consists of 5-amino salicylic acid (120 mg) in phosphate buffer 0.02 M pH 6.5 (100 ml) and hydrogen peroxide solution 1% (1 ml).

i. Coated antibody tubes were prepared as follows: The polystyrene tubes were washed with carbonate buffer 0.05 M pH 9.5 and filled with coating solution (2 ml) properly diluted with phosphate buffer saline and kept at 4° C. for 18 hours. The tubes are stored in 0.01 M phosphate, 0.15 M saline pH 7.4 (PBS) at 4° C. and can be kept in this manner for at least 6 months with no loss of activity.

3. The Assay:

To perform the enzyme immunoassay, 1 ml solution of buffer containing estradiol standards (5, 15, 50, 150, 500, 1,000 pg/ml) and 300 pg/ml estradiol-DNP conjugate is incubated for 2 hours at 37° C. in antibody coated tubes. In the blank tube only buffer solution is applied, and in the "zero" tube no estradiol standard is added, only 300 pg/ml of hapten conjugate in buffer solution. After 2 hours incubation, the solutions are decanted, the tubes rinsed with buffer PBS and 1 ml of reagent peroxidase anti-DNP conjugate diluted 1:1,000 is added into each tube and incubated for 2 hours at room temperature.

The solutions are removed by aspiration, the tubes washed thoroughly twice with PBS 0.02% Tween 20 and twice with water. Then 1 ml of substrate solution is added into each tube, and enzymatic reaction is allowed to proceed for 30-60 minutes. The enzymatic reaction is stopped by addition of 0.1 ml 0.1 N NaOH aolution. The absorbance is read at 450 nm, and the OD readings are plotted on semi-log paper versus increasing concentrations of estradiol in picograms/ml.

4. Results:

The standard curve covers the range of 5 pg/ml to 1000 pg/ml of estradiol competing with 300 pg/ml of estradiol-DNP antigen to antibody sites on polystyrene surface.

Table I is the inhibition curve as direct colorimetric readings of absorbance versus concentrations of estradiol or estradiol oxime present in the sample.

Table II shows percent of total enzymatic activity found bound to coated tubes as result of inhibition by estradiol or estradiol oxime.

The slope of the reaction is strongly affected by the affinity constants of both antigens to antiserum used for coating the polystyrene tubes and by quality of peroxidase specific reagent used.

The substitution degree of hapten conjugate is of critical importance to the assay. In principle, the optimal conditions represent compromise between the ease of detection of the macromolecule or small molecule portion of hapten conjugate and the sensitivity of the immunological system on the solid phase.

EXAMPLE 2: Determination of Estradiol Based on Estradiol-6-Carboxymethyl Oxime Ovalbumin 1. Assay description A quantity of estradiol-6-CMO-ovalbumin conjugate is added to a sample containing estradiol and the mixture is incubated in a polystyrene tube that has been coated with anti-estradiol. The amount of estradiol-6-CMO-ovalbumin bound to the tube is inversely proportional to the amount of estradiol in the sample. The actual quantity of estradiol-6-CMO-ovalbumin is determined through the use of peroxidase labeled anti-ovalbumin antibodies, followed by addition of peroxidase substrate and colorimetric readings.

EXAMPLE 3: Determination of Estradiol Based on Estradiol-6-Carboxymethyl Oxime Lysozyme 1. Assay description A quantity of estradiol-6-CMO-lysozyme conjugate is added to a sample containing estradiol and the mixture is incubated in polystyrene tube that has been coated with anti-estradiol. The amount of estradiol-6-CMO-lysozyme bound to the tube is inversely proportional to the amount of estradiol in the sample. The actual quantity of estradiol-6-CMO lysozyme bound to the tube is inversely proportional to the amount of estradiol in the sample. The actual quantity of estradiol-6-CMO-lysozyme is determined through the use of peroxidase labeled anti-lysozyme antibodies, followed by addition of peroxidase substrate and colorimetric readings.

EXAMPLE 4: Determination of Estradiol Based on Estradiol-6-Carboxymethyl Oxime Arsanil Tyrosine 1. Assay description A quantity of estradiol-6-CMO-arsanil tyrosine conjugate is added to a sample containing estradiol and the mixture is incubated in polystyrene tubes coated with anti-estradiol. The amount of estradiol-6-CMO-arsanil tyrosine bound to the tube is inversely proportional to the amount of estradiol in the sample. The actual quantity of estradiol-6-CMO-arsanil tyrosine is determined through the use of peroxidase labeled anti-arsanil antibodies, followed by addition of peroxidase substrate and colorimetric readings.

EXAMPLE 5: Determination of Serum Thyroxine

1. Materials a. The antigen $T_4$BSA for production of anti-thyroxine serum was prepared from thyroxine pentahydrate, sodium salt (Signma, USA) 50 mg and bovine serum albumin 100 mg, using 135 mg 1-ethyl-3(3-dimethylaminopropyl) carbodiimide hydrochloride for conjugation. The characterization and evaluation of the conjugate has been done spectrophotometrically by recording the U.V. absorption spectra of thyroxine residue at 324 nm and of protein molecule at 280 nm, and the ratio of 20 thyroxine residues for 1 molecule of BSA has been found. The product was used for immunization.

b. The anti-thyroxine serum was prepared by immunization of rabbits in the following manner: 2.5 mg of antigen $T_4$-BSA in saline solution with 0.5 ml Bordetella Pertusis in complete Freund's adjuvant 2.5 ml was injected intradermally. Booster injections were administered 3½ months after primary immunization and at one month intervals thereafter using the same quantities of antigen mixture, without Bordetella Pertusis addition. Major bleedings were performed 7–12 days after injections.

c. The gamma globulin fraction of anti-thyroxine serum was isolated by ammonium sulfate precipitation followed by DEAE cellulose chromatography and purified from anti-BSA antibodies by immunoadsorption on BSA agarose columns (6 mg/ml). The purified fraction of anti-thyroxine is used in the assay as coating solution for preparation of antibody coated polystyrene surface.

d. Horseradish peroxidase conjugate of anti-BSA serum was prepared from lgG fraction of anti-BSA serum (Miles 65-111) and horseradish peroxidase (Miles 36-451) by conjugation with glutaraldehyde. The peroxidase conjugate was purified on Sephadex G-200 columns and the molar ratio of gamma globulin to the enzyme was determined by U.V. absorption. The conjugate used in the assay had the molar ratio 1:1.

e. Polystyrene tubes (75×12 mm, Lab-Tek, Cat. #4411) are used as solid support.

f. Thyroxine pentahydrate, sodium salt (Sigma) is used as standard antigen.

g. Substrate used for enzymatic reaction consists of 5-amino-salicylic acid (120 mg) in phosphate buffer 0.02 M pH 6.5 (100 ml) and hydrogen peroxide solution 1% (1 ml).

h. Coated tubes are prepared as follows: the polystyrene tubes are washed with carbonate buffer 0.05 M pH 9.5 and filled with coating solution (2 ml) properly diluted with phosphate buffer saline and kept at 4° C. for 18 hours. The tubes are stored in 0.01 M phosphate, 0.15 M saline pH 7.4 (PBS) at 4° C. and can be kept in this manner for at least 6 months with no loss of activity.

2. Assay description

A quantity of thyroxine-BSA conjugate is added to a sample containing thyroxine and the mixture is incubated in a polystyrene tube that has been coated with anti-thyroxine antibodies. The amount of thyroxine-BSA bound to the tube is inversely proportional to the amount of free thyroxine in the sample. The actual quantity of thyroxine-BSA is determined through the use of peroxidase labeled anti-BSA antibodies, followed by addition of peroxidase substrate and colorimetric reading.

EXAMPLE 6: Determination of Serum Progesterone

1. Materials a. The antigen for production of anti-progesterone serum was prepared by coupling progesterone-11α-hemisuccinate 50 mg with bovine serum albumin 200 mg, using 200 mg 1-ethyl-3-(3-dimethylaminoproply)carbodiimide hydrochloride for conjugation. The characterization and evaluation of the conjugate progesterone-11α-BSA was done spectrophotometrically by recording the U.V. absorption spectra of progesterone residue at 240 nm and of bovine serum albumin at 280 nm, and the ratio of 24 progesterone residues for 1 molecule of BSA has been found. The product was used for immunization.

b. The anti-progesterone-11α-BSA serum was prepared by immunization of rabbits in the following manner: 2.5 mg of antigen progesterone-11α-BSA in saline solution with 0.5 ml Bordetella Pertusis in complete Freund's adjuvant 2.5 ml was injected intradermally. Booster injections were administered 3½ months after primary immunization and at one month intervals thereafter using the same quantities of antigen mixture, without Bordetella Pertusis addition. Major bleedings were performed 7–12 days after injections.

c. The gamma globulin fraction of anti-progesterone serum was isolated by ammonium sulfate precipitation followed by DEAE cellulose chromatography and purified from anti-BSA antibodies by immunoadsorption on BSA-agarose columns (6 mg/ml). The purified fraction of anti-progesterone is used in the assay as coating solution for preparation of antibody coated polystyrene surface.

d. Horseradish peroxidase conjugate of anti-BSA serum was prepared from 1 gG fraction of anti-BSA serum (Miles 65-111) and horseradish peroxides (Miles 36-451) by conjugation with glutaraldehyde. The peroxidase conjugate was purified on Sephadex G-200 columns and the molar ratio of gamma globulin to the enzyme was determined by U.V. absorption. The conjugate used in the assay had the molar ratio 1:1.

e. Polystyrene tubes (75×12 mm, Lab-Tek, Cat. #4411) are used as solid support.

f. Progesterone (Ikapharm, Code #2680) is used as standard antigen.

g. Substrate used for enzymatic reaction consists of 5-amino-salicylic acid (120 mg) in phosphate buffer 0.02 M pH 6.5 (100 ml) and hydrogen peroxide solution 1% (1 ml).

h. Coated tubes are prepared as follows: the polystyrene tubes are washed with carbonate buffer 0.05 M pH 9.5 and filled with coating solution (2 ml) properly diluted with phosphate buffer saline and kept at 4° C. for 18 hours. The tubes are stored in 0.01 M phosphate, 0.15 M saline pH 7.4 (PBS) at 4° C. and can be kept in this manner for at least 6 months with no loss of activity.

2. Assay description

A quantity of progesterone-BSA conjugate is added to a sample containing progesterone and the mixture is incubated in a polystyrene tube that has been coated with anti-progesterone antibodies. The amount of progesterone-BSA bound to the tube is inversely proportional to the amount of free progesterone in the sample. The actual quantity of progesterone-BSA is determined through the use of peroxidase labeled anti-BSA antibodies, followed by the addition of peroxidase substrate and colorimetric readings.

EXAMPLE 7: Determination of Prostaglandin $F_{2\alpha}$

1. Materials a. The antigen for preparation of anti-prostaglandin $F_{2\alpha}$-BSA serum was prepared by coupling of prostaglandin $F_{2\alpha}$ (20 mg) and bovine serum albumin 80 mg using 80 mg 1-ethyl-3-(3-dimethylaminopropyl) carbodiimide hydrochloride for conjugation. The final product was evaluated by U.V. absorption, taking spectra of BSA at 280 nm and by tracing the conjugate with tritiated prostaglandin $F_{2\alpha}$ (5, 6, 8, 9, 11, 12, 14, 15 $^3H$) N.E.N. NET-433. 15 residues of prostaglandin $F_{2\alpha}$ were found to be bound per BSA molecule. The product was used for immunization.

b. The anti-prostaglandin $F_{2\alpha}$-BSA serum was prepared by immunization of rabbits in the following manner: 2.5 mg of antigen prostaglandin $F_{2\alpha}$-BSA in saline solution with 0.5 ml Bordetella Pertusis in complete Fruend's adjuvant 2.5 ml was injected intradermally. Booster injections were administered 3½ months after primary immunization and at one month intervals thereafter using the same quantities of antigen mixture, without Bordetella Pertussis addition. Major bleedings were performed 7–12 days after injections.

c. The gamma globulin fraction of anti-prostaglandin $F_{2\alpha}$ serum was isolated by ammonium sulfate precipitation followed by DEAE cellulose chromatography and purified from anti-BSA antibodies by immunoadsorption on BSA-agarose columns (6 mg/ml). The purified fraction of anti-prostaglandin $F_{2\alpha}$ is used in the assay as coating solution for preparation of antibody coated polystyrene surface.

d. Horseradish peroxidase conjugate of anti-BSA serum was prepared from 1 g fraction of anti-BSA serum (Miles 65-111) and horseradish peroxidase (Miles 36-451) by conjugation with glutaraldehyde. The peroxidase conjugate was purified on Sephadex G-200 columns and the molar ratio of gamma globulin to the enzyme was determined by U.V. absorption. The conjugate used in the assay had the molar ratio 1:1.

Polysterene tubes (75×12 mm, Lab-Tek, Cat. #4411) are used as solid support.

f. Prostaglandin $F_{2\alpha}$ (a gift from Dr. F. Kohen) is used as standard antigen.

g. Substrate used for enzymatic reaction consists of 5-amino-salicyclic acid (120 mg) in phosphate buffer 0.02 M pH 6.5 (100 ml) and hydrogen peroxide solution 1% (1 ml).

h. Coated tubes are prepared as follows: the polystyrene tubes are washed with carbonate buffer 0.05 M pH 9.5 and filled with coating solution (2 ml) properly diluted with phosphate buffer saline and kept at 4° C. for 18 hours. The tubes are stored in 0.01 M phosphate, 0.15 M saline pH 7.4 (PBS) at 4° C. and can be kept in this manner for at least 6 months with no loss of activity.

2. Assay description

A quantity of prostaglandin $F_{2\alpha}$-BSA conjugate is added to a sample containing prostaglandin $F_{2\alpha}$ and the mixture is incubated in a polystyrene tube that has been coated with anti-prostaglandin $F_{2\alpha}$ antibodies. The amount of prostaglandin $F_{2\alpha}$-BSA bound to the tube is inversely proportional to the amount of free prostaglandin $F_{2\alpha}$-BSA in the sample. The actual quantity of prostaglandin $F_{2\alpha}$-BSA is determined through the use of peroxidase labeled anti-BSA antibodies, followed by addition of peroxidase substrate and colorimetric reading.

TABLE I

The results of enzyme immunoassay of estradiol performed on antibody coated tubes, shown as means of direct colorimetric readings of absorbance at 450 nm.

| Antigen concentration | OD 450 nm (background substracted) |
|---|---|
| Estradiol-6-CMO zero | 0.632 |
| 5 pg/ml | 0.594 |
| 15 pg/ml | 0.450 |
| 50 pg/ml | 0.402 |
| 150 pg/ml | 0.332 |
| 500 pg/ml | 0.204 |
| 1000 pg/ml | 0.152 |
| Estradiol zero | 0.608 |
| 12.5 pg/ml | 0.432 |
| 25 pg/ml | 0.354 |
| 50 pg/ml | 0.275 |
| 100 pg/ml | 0.191 |
| 250 pg/ml | 0.130 |
| 500 pg/ml | 0.106 |

TABLE II

The results of E.I.A. of estradiol, shown as mean percent of total enzymatic activity found bound to coated tubes as result of inhibition by estradiol or estradiol oxime.

| Antigen concentration | Percent of bound enzymatic activity $E/E_o \times 100$ |
| --- | --- |
| Estradiol-6-CMO zero | 100 |
| 5 pg/ml | 94 |
| 15 pg/ml | 71 |
| 50 pg/ml | 64 |
| 150 pg/ml | 52 |
| 500 pg/ml | 32 |
| 1000 pg/ml | 24 |
| Estradiol zero | 100 |
| 12.5 pg/ml | 83 |
| 25 pg/ml | 71 |
| 50 pg/ml | 56 |
| 100 pg/ml | 39 |
| 250 pg/ml | 20 |
| 500 pg/ml | 17 |

We claim:

1. A quantitative assay method for the determination of an unknown quantity of a hapten, hereinafter designated hapten X, which method comprises:
   a. preparing a conjugate of the hapten X which conjugate is adapted to ellicit antibody formation, and injecting a mammal with said conjugate so as to result in a specific antibody against said hapten, anti-X;
   b. preparing a conjugate of the hapten X and of another entity Y, which is either another hapten or a larger molecule;
   c. injecting a mammal with the entity Y if it is a larger molecule, or with a conjugate thereof if it is a small molecule which does not by itself ellicit antibody formation, so as to form anti-Y antibodies;
   d. preparing a conjugate of an enzyme and the antibody against Y to form enzyme-labelled anti-Y antibody;
   e. adsorbing the anti-X antibodies on a solid support;
   f. contacting said solid support with a mixture containing the unknown quantity of hapten X and a known quantity of the X-Y conjugate so as to cause all anti-X sites to be occupied;
   g. removing unreacted X and X-Y, leaving all anti-X sites occupied;
   h. contacting the support carrying occupied anti-X sites with enzyme-labelled anti-Y antibody;
   i. contacting the resulting support carrying occupied anti-X-sites and enzyme-labelled anti-Y antibody with a substrate for the enzyme which when acted upon by the enzyme produces a color reaction and measuring the resulting intensity of color so as to determine the quantity of bound enzyme and deducing from calibration curve the quantity of the hapten X.

2. An assay method according to claim 1, wherein the hapten which is being determined is a hormone, vitamin, cardiac glycoside, or polypeptide.

3. An assay method according to claim 2, wherein the hapten is selected from the group consisting of estradiol, progesterone, prostaglandin, thyroxine, and triiodothyronine.

4. An assay method according to claim 1 wherein said hapten is a drug.

5. An assay method according to claim 1, wherein the entity Y is selected from the group consisting of trinitrophenyl-lysine, sulfanilic acid, p-amino-benzoic acid, p-azophenyl-$\beta$-lactoside, hippuric acid, iodoacetylaminobenzene-azo hippuric acid, 6-carboxypurine, 5-acetyl uracil, thymidin, uridin, dinitrophenyl lysine and arsanil tyrosine.

6. An assay method according to claim 1, wherein the enzyme is a peroxidase.

7. An assay method according to claim 6, wherein the peroxidase is horseradish peroxidase.

8. An assay method according to claim 1, wherein the solid support is a polymeric substance.

9. An assay method according to claim 8, wherein the support is polystyrene.

10. An assay method according to claim 1, wherein the support is in the form of a test tube and step e comprises coating the inside of the test tubes with the anti-X antibodies.

11. An assay method according to claim 10, wherein the support is a polystyrene test tube.

* * * * *